(12) United States Patent
Jang et al.

(10) Patent No.: US 10,578,650 B2
(45) Date of Patent: Mar. 3, 2020

(54) SHUNT RESISTOR FOR MEASURING CURRENT

(71) Applicant: LG CHEM, LTD., Seoul (KR)

(72) Inventors: Dong Kwan Jang, Daejeon (KR); Ki Chan Kim, Daejeon (KR); Sang Dae Park, Daejeon (KR); Kil Ja Lim, Daejeon (KR)

(73) Assignee: LG Chem, Ltd. (KR)

( * ) Notice: Subject to any disclaimer, the term of this patent is extended or adjusted under 35 U.S.C. 154(b) by 116 days.

(21) Appl. No.: 15/711,581

(22) Filed: Sep. 21, 2017

(65) Prior Publication Data

US 2018/0113153 A1    Apr. 26, 2018

(30) Foreign Application Priority Data

Oct. 24, 2016 (KR) .................. 10-2016-0138573

(51) Int. Cl.
| | |
|---|---|
| G01R 1/20 | (2006.01) |
| H05K 3/34 | (2006.01) |
| H01C 1/144 | (2006.01) |
| G01N 27/00 | (2006.01) |
| H01C 1/00 | (2006.01) |
| H01C 7/13 | (2006.01) |
| H05K 1/18 | (2006.01) |

(52) U.S. Cl.
CPC ............ *G01R 1/203* (2013.01); *G01N 27/00* (2013.01); *H01C 1/00* (2013.01); *H01C 1/144* (2013.01); *H01C 7/13* (2013.01); *H05K 1/181* (2013.01); *H05K 3/3431* (2013.01); *H05K 2201/10022* (2013.01); *Y02P 70/613* (2015.11)

(58) Field of Classification Search
CPC ...... G01R 1/203; H05K 3/3431; G01N 27/00; H01C 1/00
See application file for complete search history.

(56) References Cited

U.S. PATENT DOCUMENTS

| | | | |
|---|---|---|---|
| 9,395,396 B2 | 7/2016 | Kageyama et al. | |
| 10,161,968 B2 * | 12/2018 | Nakamura | ........... G01R 15/146 |
| 2002/0017914 A1 * | 2/2002 | Roggel | .............. G01R 1/06738 |
| | | | 324/754.2 |
| 2002/0053734 A1 * | 5/2002 | Eldridge | ............. B23K 20/004 |
| | | | 257/724 |
| 2009/0121362 A1 * | 5/2009 | Jang | .................... H01L 23/3107 |
| | | | 257/782 |
| 2009/0224768 A1 * | 9/2009 | Dollansky | ............. G01R 1/203 |
| | | | 324/426 |

(Continued)

FOREIGN PATENT DOCUMENTS

| | | |
|---|---|---|
| JP | 2004103943 A | 4/2004 |
| JP | 2010135518 A | 6/2010 |

(Continued)

*Primary Examiner* — Dominic E Hawkins
(74) *Attorney, Agent, or Firm* — Lerner, David, Littenberg, Krumholz & Mentlik, LLP

(57) ABSTRACT

Disclosed is a shunt resistor for measuring current, and a shunt resistor for measuring current, in which one or more protrusions having an unevenness shape, which are formed on one lateral surface of a shunt resistor and one or more solders are bonded to each other, respectively and the shunt resistor and a printed circuit board are electrically connected to each other to measure current of a battery through a shunt resistance included in the shunt resistor unit.

6 Claims, 4 Drawing Sheets

(56) References Cited

U.S. PATENT DOCUMENTS

| | | | |
|---|---|---|---|
| 2012/0081055 A1* | 4/2012 | Choi | B62D 5/0406 318/432 |
| 2013/0256850 A1* | 10/2013 | Danny | H01L 23/66 257/664 |
| 2014/0063766 A1* | 3/2014 | Otremba | H01L 23/3121 361/783 |
| 2014/0327444 A1* | 11/2014 | Aparicio Rollan | G01R 31/364 324/426 |
| 2017/0212150 A1* | 7/2017 | Kang | G01R 1/203 |

FOREIGN PATENT DOCUMENTS

| | | |
|---|---|---|
| JP | 5298336 B2 | 9/2013 |
| KR | 10-1374381 B1 | 3/2014 |
| KR | 10-2015-0014218 A | 2/2015 |
| KR | 10-2015-0018641 A | 2/2015 |

\* cited by examiner

130

SHUNT RESISTOR FOR MEASURING CURRENT

CROSS-REFERENCE TO RELATED APPLICATIONS

This application claims priority to and the benefit of Korean Patent Application No. 10-2016-0138573 filed in the Korean Intellectual Property Office on Oct. 24, 2016, the entire contents of which are incorporated herein by reference.

TECHNICAL FIELD

The present invention relates to a shunt resistor for measuring current, and to a shunt resistor for measuring current, in which one or more protrusions an unevenness shape, which are formed on one lateral surface of a shunt resistor unit and one or more solders are bonded to each other, respectively and the shunt resistor and a printed circuit board are electrically connected to each other to measure current of a battery through a shunt resistance included in the shunt resistor unit.

BACKGROUND ART

A secondary battery which is high in application easiness according to a product group and has electrical characteristics including high energy density, and the like is universally applied to an electric vehicle (EV) driven by an electric driving source, a hybrid vehicle (HV) or an energy storage system (ESS) or an uninterruptible power supply (UPS) system using a medium/large battery used for a house or an industry as well as a portable device.

The secondary battery has received public attention as a new energy source for promoting eco-friendly performance and energy efficiency in that byproducts are not generated at all according to the use of the energy as well as a primary advantage of dramatically reducing the use of fossil fuels.

When the secondary battery is implemented as a battery of a portable terminal, or the like, it may not particularly be applied as above, but the battery applied to the electric vehicle or an energy storage source is used in a type in which a plurality of unit secondary battery cells is generally aggregated and used to increase suitability for a high-capacity environment.

When the plurality of unit secondary battery cells is aggregated and used, a problem may occur in which a unit cell is swollen and broken due to overheat, etc., in the case where an operation abnormality such as the flow of overcurrent, etc. occurs, and as a result, it should be considered that overcharging or overdischarging needs to be prevented from being applied to the unit cells by continuously measuring and monitoring various state values of voltages, temperatures, and the like of respective individual cells.

In the related art, the voltage and the current of a secondary battery module are measured and a shunt resistor for measuring current, which is connected to a busbar or a resistor connection unit is used while being connected to printed circuit boards (PCBs) 13 included in the secondary battery module and a secondary battery pack in order to determine overvoltage and overcurrent states through the measured voltage and current. In the related art, as illustrated in FIG. 1, a structure in which a banding type shunt resistor is mounted on the PCB 13 and a jig 14 is attached on the bottom of a resistor connection body 12 close to the shunt resistance 11 is used. In this case, since a resistance value of the shunt resistance 11 varies according to attachment locations of the jig 14 and the resistor connection body 12, the resistance value is not constant and an error occurs. As a result, it may be difficult to accurately diagnose a state of a battery based on current and voltage values measured from the shunt resistance 11.

Therefore, it is necessary to select an accurate location to be connected with a printing pattern of the PCB and reliability of the voltage and the current of the battery, which are measured from the shunt resistance 11 needs to be increased by preventing the resistance value of the shunt resistance 11 from being varied due to a component for connection with the PCB 13 through the selection of the accurate location.

SUMMARY OF THE INVENTION

The present invention has been made in an effort to provide a shunt resistor for measuring current, which is bonded onto one lateral surface of a shunt resistor unit and the shunt resistor and a printed circuit board are thus electrically connected to each other to prevent a resistance value of a shunt resistance from being varied according to a jig in the related art.

The present invention has also been made in an effort to provide a shunt resistor for measuring current, which can select an accurate location to be connected with a printing pattern of a PCB by forming one or more protrusions at a location to be connected with the PCB on one lateral surface of a shunt resistor unit.

An exemplary embodiment of the present invention provides a shunt resistor for measuring current, including: a shunt resistor unit connecting one or more terminals formed in one or more batteries and having a resistance value for measuring current of the one or more batteries; a printed circuit board (PCB) electrically connected with the shunt resistor unit; one or more protrusions formed on one lateral surface of the shunt resistor unit facing the PCB; and one or more solders connecting the PCB and the shunt resistor unit, and the shunt resistor unit and the PCB may be connected by bonding the one or more solders and the one or more protrusions, respectively.

The shunt resistor unit may include a shunt resistance having the resistance value in order to measure current of the battery, and a resistor connection unit connecting the one or more terminals and the shunt resistance, and the one or more protrusions may be formed on one lateral surface of the resistor connection unit facing the PCB.

In the protrusion, one lateral surface which does not contact the shunt resistor unit may be formed in an unevenness shape, and the solder may flow between the unevennesses in a melted state and be bonded to connect the shunt resistor unit and the PCB.

The unevenness formed in the protrusion may have at least one of a polygonal shape and a semicircular shape.

The shunt resistor for measuring current may determine the quantity and types of solders based on the shape of the unevenness of the protrusion and the number of protrusions.

The protrusion may be formed on one lateral surface of the shunt resistor unit through a pressing process.

The solder may be reflow-soldered through a surface mounting technology (SMT) process to be bonded to the protrusion.

According to an exemplary embodiment of the present invention, the present invention has been made in an effort to provide a shunt resistor for measuring current, in which one or more protrusions and one or solders having an unevenness shape, which are formed on one lateral surface of a shunt resistor unit are bonded to each other, respectively and the shunt resistor unit and a printed circuit board are thus electrically connected to each other to prevent a resistance value of a shunt resistance from being varied according to a jig in the related art.

A shunt resistor for measuring current can be provided, which can select an accurate location to be connected with a printing pattern of a PCB by forming one or more protrusions at a location to be connected with the PCB on one lateral surface of a shunt resistor unit.

DETAILED DESCRIPTION

Figure 1:
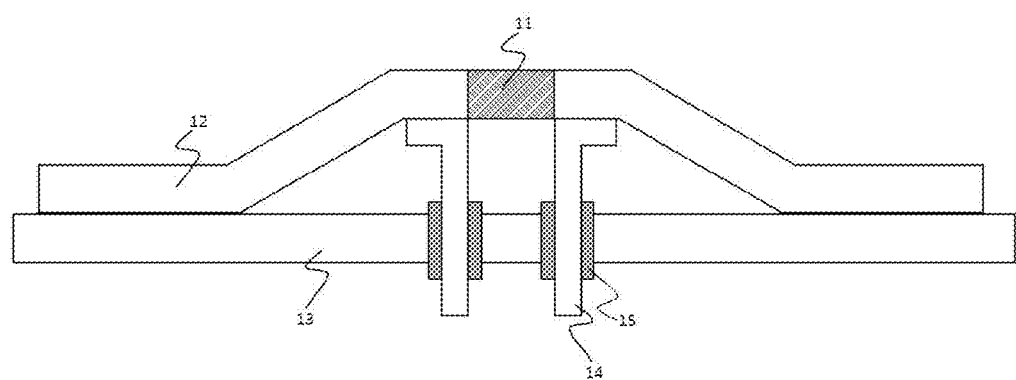
FIG. 1 is a diagram schematically illustrating a shunt resistor for measuring current in the related art.

The present invention will be described below in detail with reference to the accompanying drawings. Herein, the repeated description and the detailed description of publicly-known function and configuration that may make the gist of the present invention unnecessarily ambiguous will be omitted. Exemplary embodiments of the present invention are provided for more completely describing the present invention to those skilled in the art. Accordingly, shapes, sizes, and the like of elements in the drawings may be exaggerated for clearer explanation.

Throughout the specification, unless explicitly described to the contrary, a case where any part "includes" any component will be understood to imply the inclusion of stated components but not the exclusion of any other component.

The term "unit" disclosed in the specification means a unit that processes at least one function or operation, and the unit may be implemented by hardware or software or a combination of hardware and software.

Figure 2:
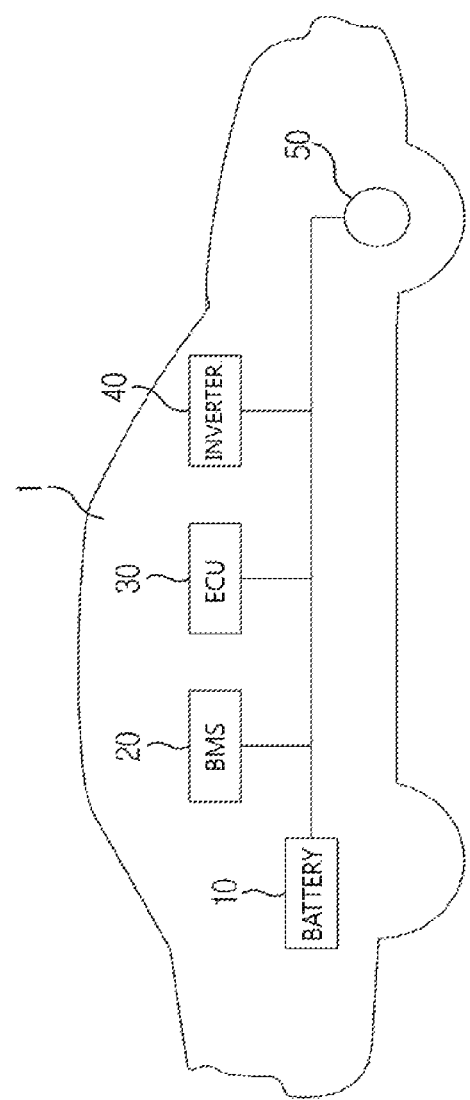
FIG. 2 is a diagram schematically illustrating an electric vehicle to which a shunt resistor for measuring current can be applied according to an exemplary embodiment of the present invention.

FIG. 2 is a diagram schematically illustrating an electric vehicle to which a shunt resistor for measuring current can be applied according to an exemplary embodiment of the present invention.

In FIG. 2, an example in which a shunt resistor 100 for measuring current according to an exemplary embodiment of the present invention is applied to an electric vehicle 1 is illustrated, but the shunt resistor 100 for measuring current according to the exemplary embodiment of the present invention may be applied to all technical fields to which a secondary battery such as a home or industrial energy storage system (ESS), or an uninterruptible power supply (UPS) system may be applied in addition to the electric vehicle.

The electric vehicle 1 may be configured to include a battery 10, a battery management system (BMS) 20, an electronic control unit (ECU) 30, an inverter 40, and a motor 50.

The battery 10 is an electric energy source that drives the electric vehicle 1 by providing driving force to the motor 50.

The battery 10 may be charged or discharged by the inverter 40 by driving the motor 50 and/or an internal combustion engine (not illustrated).

Herein, a type of battery 10 is not particularly limited and the battery 10 may be constituted by, for example, a lithium ion battery, a lithium polymer battery, a nickel cadmium battery, a nickel hydrogen battery, a nickel zinc battery, and the like.

The battery 10 is formed by a battery pack in which a plurality of battery cells is connected in series and/or in parallel. In addition, the battery 10 may include one or more battery packs.

The BMS 20 estimates the state of the battery 10 and manages the battery 10 by using estimated state information. For example, the BMS 20 estimates and manages state information of the battery 10, which includes a state of charging (SOC), a state of health (SOH), a maximum input/output power allowance amount, output voltage, and the like of the battery 10. In addition, the BMS 20 may control charging or discharging of the battery 10 by using the state information and furthermore, also estimate a replacement time of the battery 10.

The BMS 20 may include the shunt resistor 100 for measuring current according to the exemplary embodiment of the present invention to be described below or operate by connecting current and voltage measuring apparatuses to the shunt resistor 100 for measuring current. The BMS 20 may measure a charge/discharge current value of the battery by using the shunt resistance included in the shunt resistor 100 for measuring current and determine abnormal operation states such as low-voltage and overvoltage states of the battery 10 based on the measured charge/discharge current value.

The ECU 30 is an electronic control device that controls the state of the electric vehicle 1. For example, the ECU 30 determines a torque degree based on information such as an accelerator, a brake, a speed, and the like and controls an output of the motor 50 according to the torque information.

The ECU 30 transmits a control signal to the inverter 40 so that the battery 10 is charged or discharged by the BMS 20.

The inverter 40 allows the battery 10 to be charged or discharged based on the control signal of the ECU 30.

The motor 50 drives the electric vehicle 1 based on control information (e.g., torque information) transferred from the ECU 30 by using electric energy of the battery 10.

Hereinafter, referring to FIGS. 3 to 5A-5D, the shunt resistor 100 for measuring current according to the exemplary embodiment of preset invention will be described.

Figure 3:
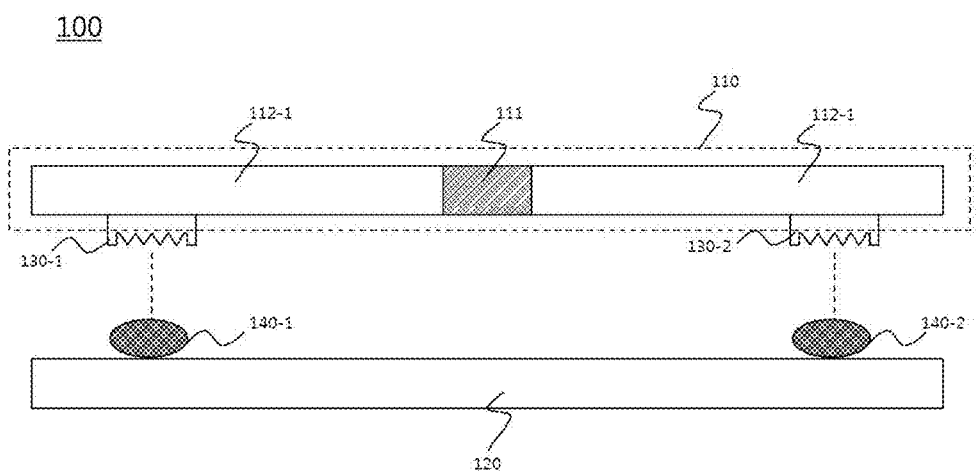
FIGS. 3 and 4 are diagrams schematically illustrating a shunt resistor for measuring current according to an exemplary embodiment of the present invention.
Figure 4:
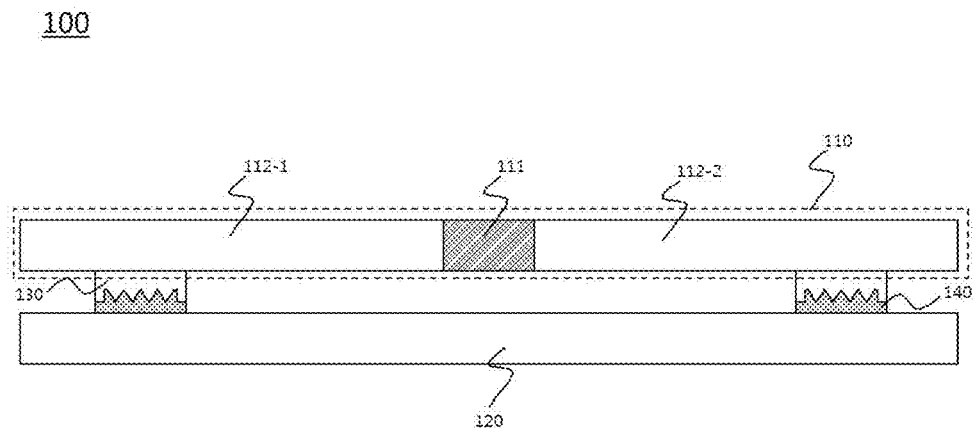
Figure 5A:
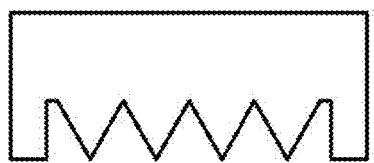
FIGS. 5A-5D are diagrams schematically illustrating a shape of a protrusion according to an exemplary embodiment of the present invention.
Figure 5B:
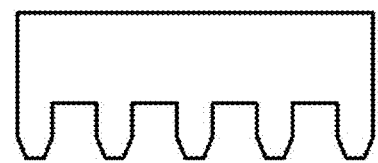
Figure 5C:
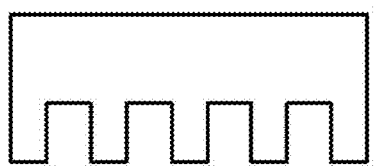
Figure 5D:
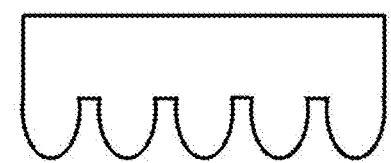

FIGS. 3 and 4 are diagrams schematically illustrating a shunt resistor for measuring current according to an exemplary embodiment of the present invention and FIGS. 5A-5D are diagrams schematically illustrating a shape of a protrusion according to an exemplary embodiment of the present invention. Referring to FIGS. 3 to 5A-5D, the shunt resistor 100 for measuring current according to the exemplary embodiment of the present invention may include a shunt resistor unit 110, a printed circuit board (PCB) 120, one or more protrusions 130, and one or more solders 140.

The shunt resistor 100 for measuring current illustrated in FIGS. 3 to 5A-5D follows the exemplary embodiment and constituent elements thereof are not limited to the exemplary embodiment illustrated in FIGS. 3 to 5A-5D and as necessary, the constituent elements may be added, modified, or deleted.

The shunt resistor unit 110 may connect one or more terminals formed in one or more batteries 10 and may have a resistance value for measuring current of one or more batteries 10. To this end, the shunt resistor unit 110 may include a shunt resistance 111 and a resistor connection unit 112.

The shunt resistance 111 may have the resistance value in order to measure the current of the battery 10. As one example, when the voltage and the current of the battery 10 are intended to be measured, whole voltage of the battery 10 may be calculated through voltage applied to both terminals of the shunt resistance 111 or the current of the battery 10 may be calculated by using an Ohm's law. For example, the resistance value of the shunt resistance 111 may be 100 uΩ. In this case, when the voltage applied to the shunt resistance 111 is 1 mV by a voltage division law, a current value of the battery 10 may be calculated by the Ohm's law (V=I*R). Further, the whole voltage of the battery 10 may be calculated through a ratio of the resistance value of the shunt resistance 111 and the resistance value of a total load.

The resistor connection unit 112 may connect one or more terminals and shunt resistors. The resistor connection unit 112 may connect one or more terminals included in one or more batteries 10, respectively. As one example, the resistor connection unit 112 may include at least one of tin (Sn), copper (Cu), nickel (Ni), zinc (Zn), and silver (Ag) and connects one or more battery (10) terminals to provide the applied voltage of the battery 10 to the shunt resistance 111.

In another exemplary embodiment, the shunt resistor unit 110 may be a busbar type. The shunt resistance 111 having the resistance value is installed on a busbar which connects each of the terminals of one or more batteries 10 to measure the current and the voltage of the battery 10 by using external current and voltage measuring elements.

The PCB 120 may be electrically connected with the shunt resistor unit 110. In the PCB 120, a conductor circuit may be formed on the surface of or in an insulation substrate in order to connect the constituent element based on a design of a circuit for driving and protecting the battery 10 in connection to one battery 10 or in connection to a plurality of or all batteries 10. Further, the PCB 120 may be used for increasing stabilities of the constituent elements related with the battery 10 by electrically connecting the constituent elements and mechanically fixing the constituent elements. Herein, in the shunt resistor 100 for measuring current according to the exemplary embodiment of the present invention, the shunt resistor unit 110 is configured to be joined to the PCB 120, but is not limited thereto and the shunt resistor unit 110 may be applied to and used in any place where the shut resistor unit 110 may be used.

In order to construct a battery state diagnosis system by using the shunt resistor 100 for measuring current according to the exemplary embodiment of the present invention, constituent elements such as an operating amplifier (OP AMP) and a micro controller unit (MCU) may be included in the PCB 120 and connected to the shunt resistor unit 110 by a protrusion 130 and a solder 140 to be described below. In this case, the voltage value of the battery 10 applied to the shunt resistance 111 is amplified by the OP AMP and the voltage value of the battery 10, which is amplified by the MCU and a reference voltage value are compared with each other to diagnose a state of the battery 10.

The protrusion 130 may be formed on one lateral surface of the shunt resistor unit 110 facing the PCB 120 and may be positioned by selecting an accurate location to be connected with a printing pattern of the PCB 120. Further, the protrusion 130 may be formed on one lateral surface of the resistor connection unit 112 included in the shunt resistor unit 110 and one or more protrusions 130 may be formed.

As one example, when the shunt resistor unit 110 and the PCB 120 are bonded to each other by the solder 140 to be described below, it may be difficult to connect the solder 140 which is in a melted state to an accurate location to be bonded with the PCB 120. Further, when the shunt resistor unit 110 and the PCB 120 are just bonded to each other by using only the solder 140, binding force is insufficient to cause a short of the circuit, and as a result, it may be difficult to measure the accurate voltage and current of the battery 10. In order to solve the difficulty, the shunt resistor 100 for measuring current according to the exemplary embodiment of the present invention forms the protrusion 130 at a location to be connected with the PCB 120 and joins the protrusion 130 and the solder 140 to be connected to the accurate location to be connected with the PCB 120. Further, the protrusion 130 may be formed with one lateral surface which does not contact the shunt resistor unit 110, which has a uneveness shape, therefore, an area which contacts the solder 140 increases to increase connection force.

When described with reference to FIGS. 5A-5D, the uneveness shape of the protrusion 130 may be formed in at least one of polygonal shapes such as a triangular shape, a rectangular shape, and a hexagonal shape or a semicircular shape as illustrated in FIGS. 5A-5D. However, the present invention is not limited thereto and the protrusion 130 may be formed in various shapes according to an environment to which the shunt resistor unit 110 is applied. The melted solder 140 may be introduced between the unevennesses of the protrusion in connecting the protrusion 130 and the solder 140, therefore, the shunt resistor unit 110 and the PCB 120 may be connected with each other by strong binding.

The protrusion 130 may be formed on one lateral surface of the shunt resistor unit 110 through a pressing process.

As one example, the protrusion 130 may include at least one of tin (Sn), copper (Cu), nickel (Ni), zinc (Zn), and silver (Ag) and the protrusion 130 of which one lateral surface has the uneveness shape is pressed to the shunt resistor unit 110 to be connected to the shunt resistor unit 110. In another exemplary embodiment, the protrusion 130 may have the uneveness shape through an etching process while being pressed and connected to the shunt resistor unit 110.

The solder 140 is reflow-soldered through a surface mounting technology (SMT) process to be bonded to the protrusion 130 and to thereby connect the PCB 120 and the shunt resistor unit 110 to each other. As one example, the solder 140 may be tin (Sn)-lead (Pb) series, tin series, lead (Pb) series, silver (Ag) series, and gold (Au) series and the solder 140 in the melted state is solidified while being bonded to the PCB 120 and the shunt resistor unit 110 to connect the PCB 120 and the shunt resistor unit 110.

The SMT process is a process of applying the solder 140 which is granulated onto the surface of the PCB 120 and mounting a part and soldering by means of a machine. In the SMT process, the PCB 120 is provided to a printer and a cream-state solder 140 which is granulated is applied to the PCB 120. Thereafter, the shunt resistor unit 110 may be positioned on the top of the PCB 120 to which the solder 140 is applied and the protrusion 130 and the solder 140 may be bonded to each other through reflow soldering. The reflow soldering is a process that melts the cream-state solder 140 applied to the PCB 120 by using heat to join the PCB 120 and the constituent element. Therefore, through the reflow soldering, the cream-state solder 140 which is applied to the PCB 120 is melted and flows between the unevenesses of the protrusion 130 and solidified to bond the PCB 120 and the constituent element.

Herein, when the quantity of the solders 140 is too small, a sufficient quantity of solders 140 do not flow between the unevennesses of the protrusion 130, and as a result, perfect bonding may not be achieved. On the contrary, when the quantity of the solders 140 is too large, the solder 140 fills a space between the unevennesses of the protrusion 130 and flows down to interrupt bonding of other constituent elements, thereby causing failure in the battery management system. Therefore, the shunt resistor 100 for measuring current according to the exemplary embodiment of the present invention may determine the quantity and types of the solders 140 based on a type of the unevenness, such as the shape and the depth of the unevenness of the protrusion 130 and the number of protrusions 130.

Hereinabove, a specific exemplary embodiment of the present invention has been illustrated and described, but the technical spirit of the present invention is not limited to the accompanying drawings and the described contents and it is apparent to those skilled in the art that various modifications of the present invention can be made within the scope without departing from the spirit of the present invention and it will be regarded that the modifications are included in the claims of the present invention without departing from the spirit of the present invention.

What is claimed is:

1. A shunt resistor assembly for measuring current, the shunt resistor assembly comprising:
   a shunt resistor unit including a resistive element having a resistance value;
   a printed circuit board (PCB) included in a battery module and electrically connected with the shunt resistor unit to provide a voltage value of the battery module to the resistive element to measure current of the one or more batteries included in a battery module based on the resistive value of the resistive element, wherein the shunt resistor unit is connected to first and second terminals formed in the one or more batteries;
   first and second protrusions formed on a lateral surface of the shunt resistor unit facing the PCB and connected to the first and second terminals, respectively, wherein each of the first and second protrusions is formed in an uneven shape having crevices; and
   first and second solder connections connecting the first and second terminals of the PCB to the first and second protrusions formed on the shunt resistor unit, respectively, wherein the first and second solder connections, when in a melted state, flow between the crevices of the first and second protrusions in order to bond to and connect the shunt resistor unit to the PCB.

2. The shunt resistor of claim 1, wherein the crevices formed in the protrusion has at least one of a polygonal shape or a semicircular shape.

3. The shunt resistor of claim 2, wherein a quantity and type of solder included in the first and second solder connections is selected based on a shape of the crevices in the first and second protrusions.

4. The shunt resistor of claim 1, wherein the first and second protrusions are formed on the lateral surface of the shunt resistor unit through a pressing process.

5. The shunt resistor of claim 1, wherein the first and second solder connections are formed by reflow-soldering through a surface mounting technology (SMT) process for bonding the PCB to the first and second protrusions.

6. The shunt resistor of claim 1, wherein the PCB is configured to diagnose a state of the battery module based on the measured current of the one or more batteries.

* * * * *